US006742528B2

(12) United States Patent
Dave

(10) Patent No.: US 6,742,528 B2
(45) Date of Patent: Jun. 1, 2004

(54) MONOFILAMENT TAPE

(76) Inventor: Vipul Bhupendra Dave, 20 Francis Dr., Hillsborough, NJ (US) 08844

( * ) Notice: Subject to any disclaimer, the term of this patent is extended or adjusted under 35 U.S.C. 154(b) by 0 days.

(21) Appl. No.: 10/287,204

(22) Filed: Nov. 4, 2002

(65) Prior Publication Data

US 2003/0150473 A1 Aug. 14, 2003

Related U.S. Application Data

(63) Continuation of application No. 09/728,127, filed on Dec. 1, 2000.

(51) Int. Cl.[7] ................................................. A61C 15/00
(52) U.S. Cl. ........................................ 132/321; 132/323
(58) Field of Search ................................. 132/321, 323, 132/324, 325, 326, 327, 328, 329; 428/339, 370, 373

(56) References Cited

U.S. PATENT DOCUMENTS 5,601,775 A * 2/1997 Cunningham et al. ...... 264/469

* cited by examiner

Primary Examiner—John J. Wilson
Assistant Examiner—Robyn Kieu Doan

(57) ABSTRACT

A bicomponent monofilament tape wherein the tape is made from the fusion of the sheaths of at least about 60 bicomponent core-sheath fibers and the bonding of the fused sheaths to the core fibers is disclosed. A process for preparing a bicomponent monofilament tape by providing at least about 60 bicomponent core-sheath fibers; fusing the sheaths; and bonding the fused sheaths to the core fibers is also disclosed.

32 Claims, 3 Drawing Sheets

MONOFILAMENT TAPE

Figure 1:
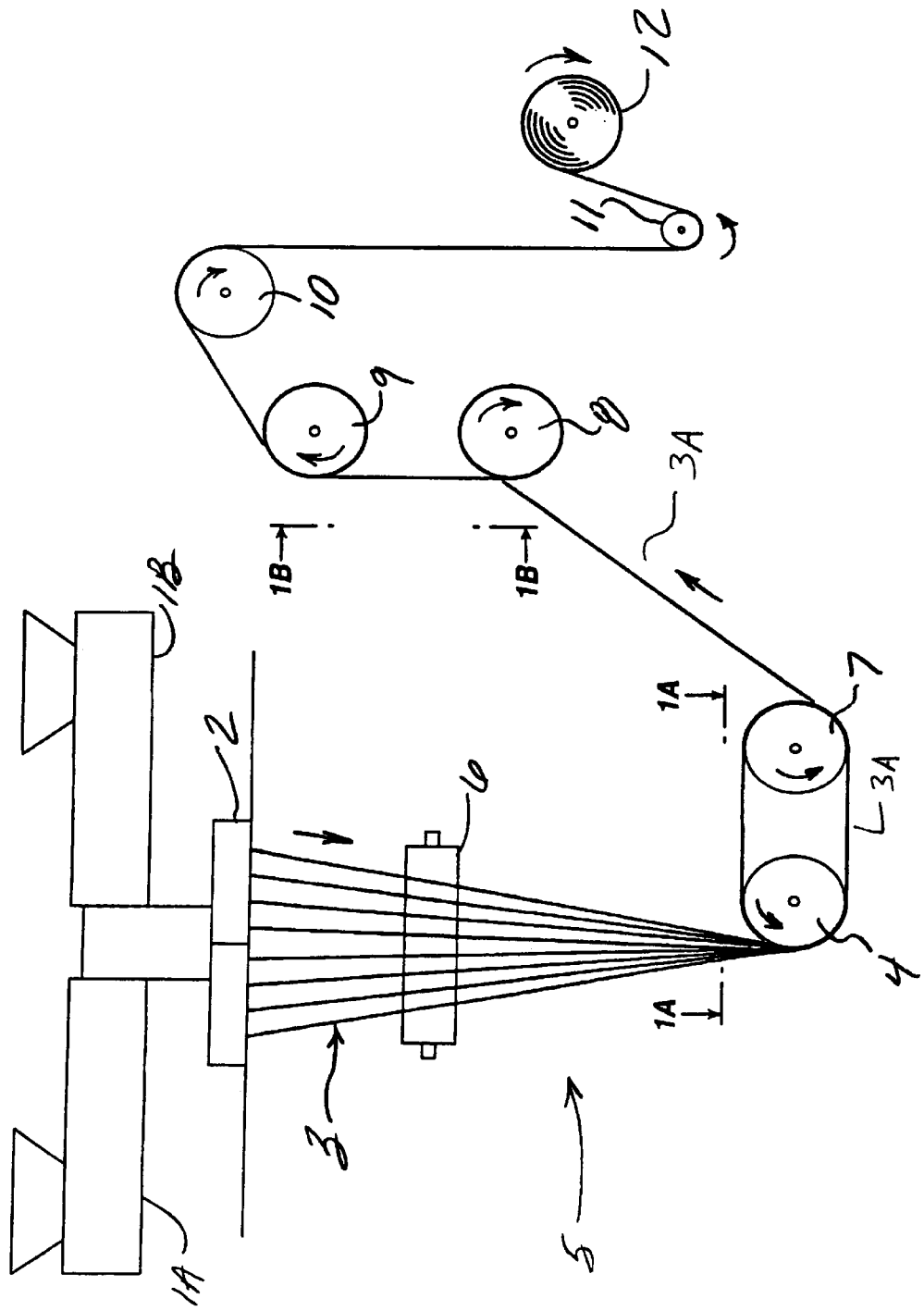

This application is a continuation of U.S. Ser. No. 09/728,127, filed Dec. 1, 2000.

The present invention relates to a monofilament tape, which may be used as a dental floss. The floss is easy to slide between the teeth, effective at cleaning, gentle to the gums, and capable of carrying more flavor than comparable flosses.

The use of dental floss is recommended by virtually all dental health practitioners. Dental flossing has been shown to be effective in removing interdental plaque according to the Council on Dental Therapeutics. Despite these facts, only about 12% of the United States population use floss regularly. Of those who do use floss, consumers prefer flosses which are shred and fray resistant, pass easily between tight teeth, are gentle to the gums, refreshen the mouth, clean effectively, and are easy to use. Mouth freshening is controlled through the use of coatings, which typically comprise flavors, mouth fresheners, cleaning agents, polishing agents and the like. The more coating the floss substrate can carry, the better the floss may be at mouth freshening and cleaning.

Monofilament flosses made from poly (tetrafluoroethylene)/("PTFE") provide most of the attributes discussed above, except for the ability to carry more flavor and other additives, and ease of handling. Many consumers feel that PTFE monofilament floss does not clean as well as conventional multi-filament flosses. In addition, the cost of PTFE floss is relatively high, mainly due to the high resin cost. Therefore, there is a need to replace PTFE with lower cost materials that will provide the above-mentioned consumer preferred attributes.

One technology that may be useful for dental floss applications is bicomponent fiber technology. Bicomponent fibers are fibers which are made from two different polymers. Bicomponent fibers are also known as "conjugate", "composite" or "hetero" fibers. The main advantage of using this technology is to combine polymers with different properties in a single filament. Bicomponent fibers are commonly classified by their cross-sectional structures such as core-sheath; side-by-side; islands-in-the-sea; and pie-shaped.

U.S. Pat. No. 5,845,652 discloses the preparation of core-sheath bicomponent fibers using different materials and yarn constructions. The sheath polymers are thermoplastic elastomers, such as Pebax® and Hytrel® Brand polymers, and the core polymer is nylon. The specific examples set forth in the patent are based on 70/30 core-sheath fibers made from nylon/Pebax® 2533; nylon/Hytrel® 3078 and nylon/nylon having e.g., 144 filaments; a denier ranging from 580–730; no twist and tensile strengths of 3.4–5 g/d. These fibers were flattened on heated godets to bond the sheaths of the filaments during the fiber spinning process. The patent discloses the aspects of forming bulkable floss by utilizing different materials, mainly by using side-by-side bicomponent fibers. It also teaches methods of obtaining self-bulking and tension-induced bulkable floss.

U.S. Pat. No. 5,904,152 discloses a multifilament floss which has multiple cores made from nylon with either a Hytrel® or Pebax® Brand thermoplastic elastomeric polymer as the sheath.

U.S. Pat. No. 5,875,797 discloses a multicomponent, co-extruded, monofilament dental floss comprising a core comprising a first material such as nylon. The core is embedded in a sheath comprising a second material such as a thermoplastic elastomeric polymer. The floss has a continuous outer surface. The monofilament floss is prepared by using core-sheath technology and a die assembly during the co-extrusion process. Typical flosses disclosed in this patent have a denier of 600–700 and comprise 34 filaments with a 70/30 ratio of core polymer/sheath polymer. The disclosed flosses have a tenacity of 3–4.5 g/d and an elongation of at least 300%.

Despite the disclosure of the references, there is a continuing need for a floss which is shred and fray resistant, gentle to the gums, mouth freshening, effective at cleaning, easy to use, and passes readily between tight teeth.

The present invention provides an article comprising a bicomponent monofilament tape, said bicomponent monofilament tape comprising at least about 60 individual core fibers comprising a first polymer, said individual core fibers being embedded in and substantially completely surrounded by a fused sheath comprising a second polymer.

In another aspect, the present invention provides a process which includes the steps of providing at least about 60 bicomponent core-sheath fibers and fusing the sheaths to form a monofilament tape.

The bicomponent monofilament tape of the invention is made from the fusion of the sheaths of bicomponent core-sheath fibers. The bicomponent core-sheath fibers may be made by any process known in the art, including, but not limited to, using a co-extrusion melt spinning or solution spinning process. Co-extrusion of bicomponent fibers can be defined as extruding two polymers through the same spinneret with both polymers contained within the same filament with a distinct boundary between them.

FIG. 1 is a schematic illustration of a suitable process for making bicomponent fibers. The polymers utilized to form the core and the sheath are placed in single screw extruders (1A) and (1B). The polymers are heated and melted in the extruders, then passed through a spinneret (2) to form a plurality of co-extruded bicomponent fibers (3). The co-extruded bicomponent fibers are drawn by at least one roller (4). The co-extruded bicomponent fibers (3) are cooled in the region between the spinneret and the roller (4). The cooling may be provided by means known in the art, such as, but not limited to, chilled air (5). During the co-extrusion of the bicomponent fibers, the viscosities of the two polymers at the spinneret are preferably matched in order to prevent extrudate dogleg, which is the undesirable bending of the co-extruded bicomponent fiber (3) as it exits the spinneret (2). Matching of the viscosities may be achieved through the selection of polymeric components and the control of the temperature of the polymers in the single screw extruders (1A) and (1B) and the spinneret (2).

A spin finish may be applied by a roller (6) disposed in the cooling region (5) between the spinneret (2) and the first roller (4). Suitable spin finishes include, but are not limited to, Fasavin®2830 and Fasavin® 2758, which are commercially available through Zschimmer and Schwarz.

Roller (4) draws the plurality of bicomponent fibers exiting spinneret (2), i.e. the fibers are drawn, or stretched, as they pass through cooling zone (5) toward first roller (4). The effect of this drawing or stretching step is two-fold: first the fibers are reduced in diameter (i.e., their denier is reduced) and secondly, their tensile strength is increased. As is well known, the term "denier" refers to the weight in grams per 9000 meters of fiber.

Figure 1A:
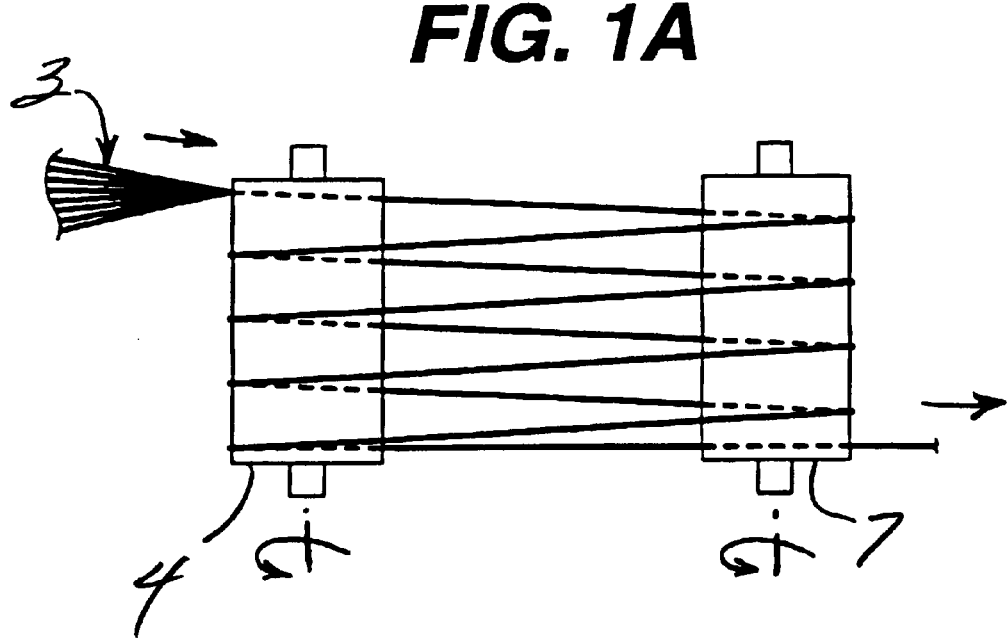

For example, at a constant rate of extrusion of polymer melt from spinneret (2), the fiber denier is reduced by increasing the rate of rotation of roller (4). Roller (4) typically rotates at a rate of from about 100 meters per minute to about 2000 meters per minute, preferably from about 400 meters per minute to about 1000 meters per minute. Preferably, a second roller (7) is used in conjunction with the first roller (4). The second roller (7) rotates at substantially the same speed as first roller (4). As can be seen by reference to FIG. 1 and FIG. 1A, the plurality of bicomponent fibers (3) are collated as they leave the lower region of the cooling zone and then come into contact with the lower surface of roller (4). The collated bicomponent fibers (3A) leave roller (4) and then come into contact with the lowermost surface (as seen in FIG. 1) of roller (7). The fibers continue to pass around roller (7) in a counterclockwise direction until they reach the uppermost surface (as seen in FIG. 1) of roller (7). The fibers are then conducted across the gap between rollers (4) and (7) and are brought into contact with the uppermost surface (as seen in FIG. 1) of roller (4). One wrap of the collated fibers is completed as the collated bundle of co-extruded fibers again reaches the point at which it first contacted roller (4) as it initially left cooling zone (5). After the completion of four such wraps around rollers (4) and (7), the collated fiber bundle (3A) leaves the lower surface (as seen in FIG. 1) of roller (7) and proceeds toward roller (8).

Figure 1B:
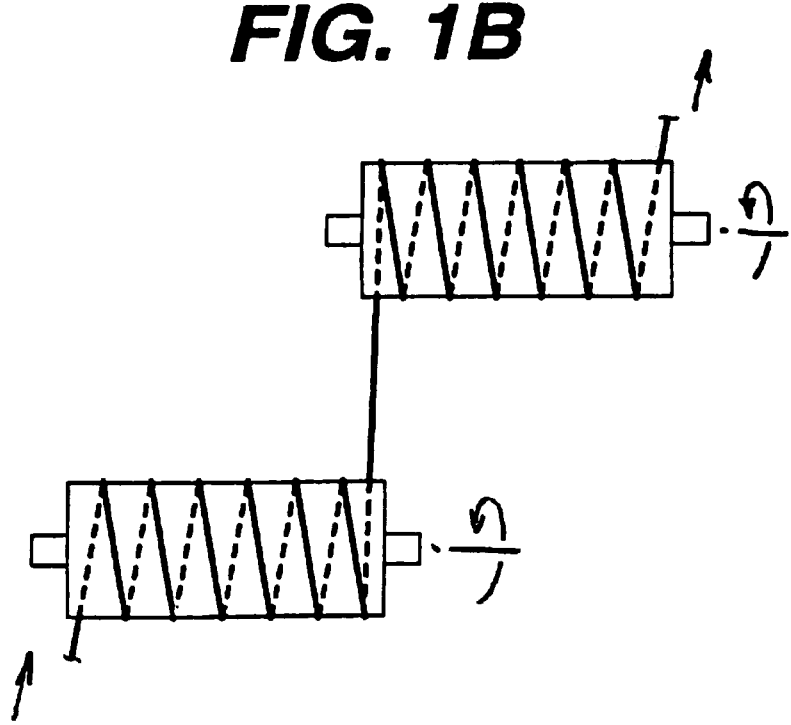

Roller (8) is set to rotate at a faster speed than that of roller (4) and (7), as a result of which the co-extruded bicomponent fibers (3) in the collated bundle (3A) are further drawn, i.e., as is well know in the art, their denier is further reduced and their tensile strength is further increased. As can be seen in FIG. 1B, collated fiber bundle (3A) wraps several times around roller (8) after which it passes to roller (9). Fiber bundle (3A) wraps several times around roller (9) before proceeding to roller (10).

Rollers (8) and (9) typically rotate at a speed of 100 meters to 3000 meters per minute, preferably at a speed of 1500 meters to 2500 meters per minute. Roller (9) should be operated at at least the same speed as roller (8). If desired, roller (9) can be operated at a faster speed than roller 8, in which case the denier of the fibers will be further reduced and their tensile strength further increased.

As mentioned, collated fiber bundle (3A) passes to roller (10) after leaving roller (9). Roller (10) is rotated at a speed which is lower than that of roller (9), as a result of which the fibers are allowed to relax. The fiber bundle (3A) passes several times around roller (10) and then passes under idle roller (11). The fiber bundle (3A) is then taken up on roller (12) to await further processing.

As is known in the art, any of the rollers (4), (7), (8), (9), and (10) may be heated. The temperatures of the heated rollers (4), (7), (8), (9), and (10) may range from about 30° C. to about 80° C., preferably from about 50° C. to about 75° C.

The bicomponent fibers utilized in the present invention are core-sheath fibers. The bicomponent fibers utilized in this invention may have cross-sectional shapes such as round; trilobal; cross; and others known in the art.

In order to be suitable for use in the present invention, the melting point of the polymer constituting the sheath component of the core-sheath bicomponent fibers must be lower than the melting point of the polymer constituting the core component. Suitable polymers for the core include polyamides such as, but not limited to, nylon 6, nylon 11, nylon 12, and nylon 66; polyesters such as, but not limited to, poly(ethylene terephthalate) ("PET") and poly(butylene terephthalate) ("PBT"); polyolefins such as, but not limited to, polypropylene and polyethylene; and fluorinated polymers, such as, but not limited to, poly(vinylidene fluoride) and mixtures thereof. Nylon 6 and polypropylene are preferred.

Suitable polymers for the sheath include polyolefins such as, but not limited to, polyethylene ("PE") and polypropylene; polyesters such as, but not limited to, polycaprolactone ("PCL"); poly(ether-amides) such as, but not limited to, Pebax® 4033 SA and Pebax® 7233 SA (Trademark of Elf Atochem); poly(ether-esters) such as, but not limited to, Hytrel® 4056 (Trademark of DuPont) and Riteflex® poly (ether-ester) polymers available through Hoechst-Celanese; elastomers made from polyolefins, for example Engage® elastomers available through DuPont Dow; poly(etherurethane) such as, but not limited to, Estane® poly(etherurethane) polymers available from BF Goodrich; poly(ester urethane) such as, but not limited to, Estane® available through BF Goodrich; Kraton® polymers such as, but not limited to poly(styrene-ethylene/butylene-styrene) available through Shell; and poly(vinylidene fluoride) copolymers, such as, but not limited to, KynarFlex® 2800, available through Elf Atochem. Pebax® 4033, polyethylene, and PCL are preferred.

The ratio of the two components of the core-sheath fibers may be varied. All ratios used herein are based on volume percents. The ratio may range from about 10 percent core and about 90 percent sheath to about 90 percent core and about 10 percent sheath, preferably from about 20 percent core and about 80 percent sheath to about 80 percent core and about 20 percent sheath, more preferably from about 30 percent core and about 70 percent sheath to about 70 percent core and about 30 percent sheath.

During the process for making the monofilament bicomponent tape of the present invention, the sheaths of the bicomponent fibers are fused. As used herein, the term "fused" means that the bicomponent fibers comprising collated bundle (3A) are exposed to a sufficient temperature for a sufficient period of time so that the sheaths of the individual core-sheath filaments (3) are completely melted and flow together to form a substantially continuous matrix of sheath material. The time and temperature conditions under which the fusion process takes place are, as would be understood by one skilled in the art, a function of the melting point of the particular polymer comprising the sheath material of the individual core-sheath fibers. The temperature at which the fusion of the sheaths of the core-sheath fibers is conducted is lower than the melting point of the cores of the core-sheath bicomponent fibers. As a result, the bicomponent monofilament tape of the present invention comprises a plurality of individual core fibers of polymeric material embedded in and substantially completely surrounded by fused sheath material. Fusion can be achieved, for example, by preheating fiber bundle 3A and then calendaring the preheated bundle. Calendaring is the passage of the fibers between the nip of two heated rollers separated by a specific gap which is set to control the thickness and width of the tape. The flexibility of the finished monofilament bicomponent tape can be controlled by the selection of suitable materials for core and sheath, by the ratio of sheath material to core material, and by the number and denier of the core-sheath filament in fiber bundle 3A.

Figure 2:
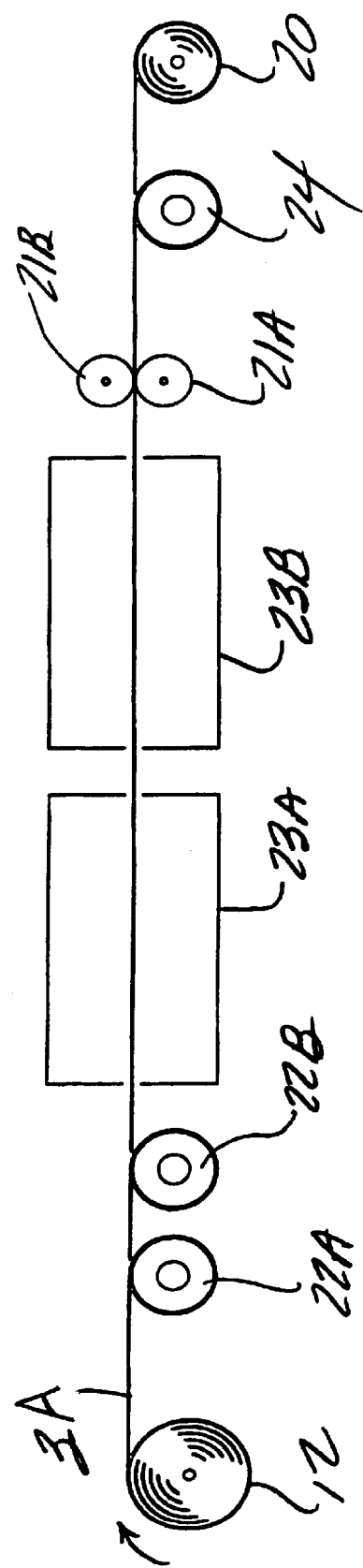

FIG. 2 is a schematic illustration of a process for converting co-extruded bicomponent fibers into the monofilament tape of the present invention. The co-extruded bicomponent fibers (3) prepared as described above are pulled by a take-up roller (20). The number of fibers (3) is at least about 60, typically from about 150 to about 500, preferably from about 200 to about 450, more preferably from about 300 to about 400. In the conversion process, the co-extruded bicomponent fibers (3) are pulled through the nip of heated rollers (21A) and (21B) by the roller (20), to thereby fuse the sheaths of the individual bicomponent fibers, thus forming a monofilament tape in accordance with the teachings of the present invention. The temperature of the rollers (21A) and (21B) may range from about 40° C. to about 90° C., preferably from about 40° C. to about 85° C.

Optionally, the fibers (3) may be pulled from the supply roll (12) (FIG. 2) over at least one heated roller (22A) prior to calendaring. In a preferred embodiment, the fibers (3) are pulled over a second heated roller (22B) prior to calendaring at rolls (21A/21B). The temperature of the heated rollers (22A) and (22B) may range from about 40° C. to about 170° C. The fibers (3) may then enter at least one oven (23A) prior to calendaring. In a preferred embodiment, the fibers enter a second oven (23B) prior to calendaring. The temperature of the ovens may range from about 110° C. to about 180° C., preferably from about 115° C. to about 170° C. The monofilament tape may be pulled over at least one roller (24) at ambient temperature to aid in cooling the tape.

The thickness of the monofilament tape may range from about 0.013 mm to about 0.15 mm, preferably from about 0.025 mm to about 0.07 mm.

The combination of the soft sheath polymer and the strength provided by the core fibers allows balancing the floss properties to provide the desired suppleness and gentleness to the gums. The sheath material can be selected such that it has high coefficient of friction and critical surface free energy so that the tape can be coated at higher amounts of wax and other additives to provide ease of handling and other desirable properties.

For dental floss applications, the monofilament tape is coated with a coating composition containing wax, flavor, and other additives to form a dental floss. The amount of wax, flavor, and other additives typically coated on fibers to make floss is known in the art. Typically, the coating composition is added at from 15 weight percent to 60 weight percent, based on the weight of the monofilament tape. Suitable flavors include, but are not limited to, natural and synthetic flavor oils, such as mint and cinnamon. The flavor oils may be used as is, or may be encapsulated or supported on a carrier such as starch or modified starch.

Other additives include, but are not limited to, sweeteners such as bulk sweeteners, including sorbital and mannitol, and intense sweeteners including aspartame and sodium saccharin, as taught by U.S. Pat. No. 6,080,481, hereby incorporated by reference for the disclosure relating to waxes and sweeteners; abrasives, such as silica; dentrifices, such as a fluoride or fluoride containing compound; chemotherapeutic agents; cleaners, such as peroxides; and whiteners. Examples of suitable additives are disclosed in U.S. Pat. No. 5,908,039, the disclosure of which is hereby incorporated by reference.

The following Examples are intended to demonstrate the monofilament tape and the process of the invention. The Examples should in no way be interpreted as limiting the scope of the invention.

EXAMPLE 1

Monofilament tapes in accordance with the teachings of the present invention were prepared using the apparatus illustrated in FIG. 2. The monofilament tapes of this Example 1 comprised a plurality of polyester core fibers embedded in a substantially continuous matrix of polyethylene sheath material. Each tape was prepared from a plurality of commercially available bicomponent fibers having a polyethylene terephthalate (PET) core and a polyethylene (PE) sheath. The starting bicomponent fibers had deniers ranging from about 1.64 to about 2.8 denier per filament. The volume ratio of PE sheath material to PET core material in the starting bicomponent fibers ranged from 20/80 PE/PET to 60/40 PE/PET. The specific gravity of the PE polymer at 210° C. was about 0.76 and the specific gravity of the PET polymer at 290° C. was about 1.19. All eleven (11) of the monofilament tape samples reported in Table 1 were made from a starting bundle of 304 PE/PET bicomponent fibers. The finished monofilament tapes reported as Samples 1–11 in Table 1 had thicknesses in the range of about 0.03 mm to about 0.05 mm. The finished monofilament tapes identified as Samples 1–4 in Table 1 had a denier of 840, which was obtained by using 304 bicomponent fibers each having a denier of about 2.76. Similarly, the finished monofilament tapes identified as Samples 5–7 in Table 1 had a denier of 700, which was obtained by using 304 starting bicomponent fibers each having a denier of about 2.3. Finished monofilament tapes identified as Samples 8–10 in Table 1 had a denier of 600, which was obtained by processing 304 starting bicomponent fibers each having a denier of about 2. Finally, the finished monofilament tape identified as Sample 11 in Table 1 had a denier of about 500, which was obtained by using 304 starting bicomponent fibers each having a denier of about 1.64.

The breaking load, tenacity and % elongation data reported in Table 1 are for the finished monofilament tapes.

The 11 monofilament tapes in accordance with the invention and as reported in Table 1 were made using the apparatus illustrated in FIG. 2. The starting bundle 3A of bicomponent fibers was taken from supply roll 12. Rollers (22A) and (22B) were spaced apart about 12 inches. Both rollers were held at a temperature of 120–125° C. and rotated at a speed of about 80 meters per minute. Oven (23A) was about 8 feet in length, spaced about 12 inches from roll (22B), and held at a temperature of 130° C. Oven (23B) was 6 feet long and was also held at a temperature of 130° C. The distance between the two ovens was about 6 inches.

A calendar was located closely adjacent the exit of oven (23B) and consisted of a pair of vertically stacked rollers 21A and 21B, both rollers being held at a temperature of about 70° C. and rotated at about 80 meters/minute. There was a slight gap between calendar rolls (21A) and (21B), this gap corresponding substantially to the desired thickness of the finished monofilament tape. Roll 24 was held at ambient temperature and was rotated at about 80 meters per minute. The tape exiting the nip of rolls (21A), (21B) was wrapped around roll 24 about 3–4 turns before proceeding to take up roll 20 operating at about 80 meters/minute. The distance between stacked calendar rolls (21A), (21B) and the exit of oven (23B) was about 6 inches.

Referring still to FIG. 2, the starting bundle 3A of bicomponent fibers was led from supply roll 12 and wrapped about 6 turns around roll 22A before proceeding to roll 22B. The fibers were wrapped about 4 turns around roll 22B before being drawn through ovens (23A), (23B). After exiting oven (23B), the fiber bundle passed through the nip of calendar rolls (21A), (21B), then for 3–4 turns around roll 24 before being wound up on take-up roll 20. Under the above described processing conditions, the residence time of the bundle of fibers on rolls (21A), (21B) was about 8 seconds. The residence time in ovens (23A), (23B) totaled approximately 3–4 seconds.

The monofilament tapes were analyzed for mechanical properties. The results are shown in the three right-hand columns of Table 1. The deniers of the various finished monofilament tapes are shown in Table 1 as well.

For all of the Examples within this patent application, denier, tenacity, breaking load, and percent elongation at break were tested following ASTM 2763 protocol.

TABLE 1

| Sample | PE/PET Ratio* | Denier | Breaking Load (lbs) | Tenacity (g/d) | Elongation (%) |
|---|---|---|---|---|---|
| 1 | 20/80 | 840 | 15.5 | 8.3 | 9.5 |
| 2 | 40/60 | 840 | 9.5 | 5.1 | 10.2 |
| 3 | 50/50 | 840 | 7.3 | 3.9 | 14.4 |
| 4 | 60/40 | 840 | 6 | 3.3 | 18.6 |
| 5 | 40/60 | 700 | 8.3 | 5.4 | 10.4 |
| 6 | 50/50 | 700 | 6.5 | 4.2 | 11.6 |
| 7 | 60/40 | 700 | 5 | 3.2 | 17.4 |
| 8 | 40/60 | 600 | 7.3 | 5.5 | 8.3 |
| 9 | 50/50 | 600 | 5.5 | 4.2 | 10 |
| 10 | 60/40 | 600 | 4.3 | 3.3 | 16 |
| 11 | 40/60 | 500 | 5.4 | 4.9 | 9.5 |

*of the individual starting bicomponent fibers

In order to obtain the proper balance between strength and suppleness in the fibers for application as a dental floss, the tenacity was plotted versus percent PE content in the fibers. The tenacity of the fibers drops exponentially with increasing the PE content. Therefore, increasing the PE content should provide a floss which is more supple.

The tenacity was measured for both the bundle of bicomponent fibers and the monofilament tape. The tenacity of the monofilament tape was consistently higher than the tenacity of the bundle of bicomponent fibers by about 6–10%.

Six additional monofilament tapes in accordance with the invention were made using the same process as that used for making Samples 1–11 in Table 1.

Two samples, 12 and 12A had a finished denier of 600. Sample 12 was made from a bundle of 152 individual PE/PET bicomponent fibers each having a denier of about 3.95, whereas Sample 12A was made from a bundle of 304 individual PE/PET bicomponent fibers each having a denier of about 2. Samples 13 and 13A had a finished denier of 650 and were made, respectively, from starting fiber bundles having 152 fibers (each about 4.2 denier/filament) and 304 fibers (each about 2.1 denier/filament). Samples 14 and 14A had a finished denier of 700. Sample 14 was made from a starting bundle of 152 bicomponent fibers each having a denier of about 4.6, while Sample 14A was made from a starting bundle of 304 bicomponent fibers each having a denier of about 2.3.

In all cases the bicomponent fibers were substantially circular in cross-section and comprised a polyethylene (PE) sheath and a polyethylene terephthalate (PET) core at a volume ratio of 45 PE/55 PET.

Breaking load and tenacity of the six finished samples are reported in Table 2.

TABLE 2

| | | Breaking Load (lbs) | | Tenacity (g/d) | |
|---|---|---|---|---|---|
| Sample | Denier | 152 Fibers | 304 Fibers | 152 Fibers | 304 Fibers |
| 12 | 600 | 7 | — | 5.3 | — |
| 12A | 600 | — | 6.5 | — | 4.9 |
| 13 | 650 | 7.1 | — | 5 | — |
| 13A | 650 | — | 6.8 | — | 4.7 |
| 14 | 700 | 7.5 | — | 4.9 | — |
| 14A | 700 | — | 7.4 | — | 4.8 |

In general, the monofilament tapes had sufficient tenacity and strength to be used as dental flosses. The monofilament tapes made from 152 bicomponent fibers were stronger than corresponding tapes prepared from 304 bicomponent fibers of the same deniers. In an effort to improve the properties of the 600 denier monofilament tape made from 152 component fibers, experiments were conducted with different amounts of PE. The results are summarized in Table 3.

TABLE 3

| Sample | % PE | B. Load (lbs) | Tenacity (g/d) |
|---|---|---|---|
| 15 | 35 | 7.4 | 5.6 |
| 16 | 40 | 7 | 5.3 |
| 17 | 45 | 6.5 | 5 |

B. Load = breaking load

The results indicate that 35% PE provided the strongest monofilament tape with a tenacity of almost 6 g/d.

The bicomponent filaments used in the following Examples 2–5 were prepared by an extrusion process illustrated schematically in FIG. 1.

For the extrusion process, the following apparatus and conditions were used: extruders: standard 3.8 cm single screw extruders with L:D=30:1 equipped with hoppers; spinnerts: 2 spinning heads with 175 hole spinnerets and 0.4 to 0.8 mm die holes; quench air temperature=6–18° C.; total draw ratio=roller (10) speed/roller (7) speed; take-up speed: 700–2500 m/min.

EXAMPLE 2

Polyolefin-Polyester (Core-Sheath)

A series of polyolefin/polyester core-sheath monofilament tapes was prepared using the extrusion equipment and coextrusion process described above with reference to FIG. 1. The core material was polypropylene ("PP") and the sheath material was polycaprolactone ("PCL"). The PCL used in this Example 2 is commercially available and was obtained from Union Carbide under the designation Tone® 767. The specific gravity of PP at 250° C. is 0.75. The PP-PCL core-sheath fibers were prepared from 80/20 to 50/50 core-sheath ratios; 175 to 350 fibers; 0.4 mm to 0.8 mm hole size; 500 to 800 denier (1.4 to 4.6 denier per fiber); 2.5 to 6 draw ratio; ambient to 50° C. draw temperature and 2 to 5.5 g/d tenacity. Fusing of the PCL sheath material to form the monofilament tape occurred between zone 5 and roller 12 in the apparatus shown in FIG. 1. The monofilament tapes were analyzed for their mechanical properties. The results are shown in Tables 4A, 4B, 5, 6A, and 6B.

TABLE 4A

| 350 Fibers Sample | Sheath PCL 767 | Core PP* | Draw Ratio | Denier | Breaking Load (lbs) | Tenacity (g/d) | Elongation (%) |
|---|---|---|---|---|---|---|---|
| 18 | 20 | 80 | 3.6 | 790 | 6.8 | 3.9 | 52 |
| 19 | 35 | 65 | 3.1 | 720 | 6 | 3.8 | 50 |
| 20 | 50 | 50 | 3.1 | 730 | 4.8 | 3 | 51 |
| 21 | 35 | 65 | 3 | 600 | 4.7 | 3.6 | 92 |
| 22 | 35 | 65 | 2.5 | 630 | 3.9 | 2.8 | 144 |
| 23 | 35 | 65 | 3 | 630 | 4.7 | 3.4 | 93 |
| 24 | 35 | 65 | 3.4 | 630 | 5.2 | 3.7 | 79 |
| 25 | 35 | 65 | 4 | 630 | 5.7 | 4.1 | 62 |
| 26 | 35 | 65 | 3.1 | 550 | 4.2 | 3.5 | 84 |

Draw Temperature = ambient
*MFR of 36 as measured by ASTM-D1238

TABLE 4B

| 350 Fibers 640 Denier | Sheath PCL 767 | Core PP* | Draw Ratio | DT | Breaking Load (lbs) | Tenacity (g/d) | Elongation (%) |
|---|---|---|---|---|---|---|---|
| 27 | 20 | 80 | 4 | 30 | 6.9 | 4.8 | 33 |
| 28 | 35 | 65 | 4 | 30 | 6 | 4.2 | 44 |
| 29 | 50 | 50 | 4 | 30 | 4.9 | 3.4 | 49 |
| 30 | 20 | 80 | 4.2 | 30 | 6.7 | 4.7 | 29 |
| 31 | 35 | 65 | 4.2 | 30 | 6.1 | 4.3 | 36 |
| 32 | 50 | 50 | 4.2 | 30 | 4.8 | 3.4 | 42 |
| 33 | 20 | 80 | 4 | 50 | 6.7 | 4.8 | 27 |
| 34 | 35 | 65 | 4 | 50 | 5.8 | 4.1 | 34 |
| 35 | 50 | 50 | 4 | 50 | 4.8 | 3.4 | 43 |
| 36 | 20 | 80 | 4.6 | 50 | 7.5 | 5.4 | 23 |
| 37 | 35 | 65 | 4.6 | 50 | 6.5 | 4.6 | 27 |
| 38 | 50 | 50 | 4.6 | 50 | 5.2 | 3.6 | 32 |

DT = draw temperature (in ° C.)
*MFR of 36 as measured by ASTM-D1238

TABLE 5

| Sample | Hole Size | Sheath | Core | Draw Ratio | Breaking Load (lbs) | Tenacity (g/d) | Elongation (%) |
|---|---|---|---|---|---|---|---|
| 39 | 0.4 mm | 20 | 80 | 5 | 6.2 | 4.7 | 40 |
| 40 | 0.6 mm | 20 | 80 | 5 | 6 | 4.5 | 40 |
| 41 | 0.8 mm | 20 | 80 | 4.5 | 5.5 | 4.2 | 55 |
| 42 | 0.4 mm | 35 | 65 | 5 | 5.5 | 4.2 | 50 |
| 43 | 0.6 mm | 35 | 65 | 5 | 5.4 | 4.1 | 51 |
| 44 | 0.8 mm | 35 | 65 | 4.5 | 5.2 | 3.9 | 64 |
| 45 | 0.8 mm | 35 | 65 | 5 | 5.5 | 4.2 | 42 |
| 46 | 0.4 mm | 50 | 50 | 5 | 4.7 | 3.6 | 57 |
| 47 | 0.6 mm | 50 | 50 | 5 | 4.6 | 3.5 | 63 |
| 48 | 0.8 mm | 50 | 50 | 4.5 | 4.7 | 3.6 | 67 |
| 49 | 0.8 mm | 50 | 50 | 5 | 4.7 | 3.6 | 48 |
| 50 | 0.4 mm | 20 | 80 | 5.5 | 6.6 | 5 | 34 |
| 51 | 0.4 mm | 35 | 65 | 5.5 | 5.6 | 4.2 | 44 |
| 52 | 0.4 mm | 50 | 50 | 5.5 | 4.7 | 3.6 | 49 |
| 53 | 0.4 mm | 50 | 50 | 6 | 5.2 | 3.9 | 30 |
| 54 | 0.6 mm | 50 | 50 | 5.5 | 4 | 3 | 47 |

Made from 175 fibers
Draw Temperature = ambient

TABLE 6A

| Sample | PCL 767 | PP* | Draw Ratio | Denier | Breaking Load (lbs) | Tenacity (g/d) | Elongation (%) |
|---|---|---|---|---|---|---|---|
| 55 | 35 | 65 | 3.1 | 730 | 4.3 | 2.7 | 128 |
| 56 | 50 | 50 | 3.1 | 730 | 3.4 | 2.1 | 140 |

Made From 350 fibers
Draw Temperature = ambient
*MFR of 18 as measured by ASTM Test Method D-1238

TABLE 6B

| Sample | PCL 767 | PP* | Draw Ratio | Denier | Breaking Load (lbs) | Tenacity (g/d) | Elongation (%) |
|---|---|---|---|---|---|---|---|
| 57 | 35 | 65 | 3 | 630 | 4.1 | 2.9 | 140 |
| 58 | 35 | 65 | 3.2 | 630 | 4.3 | 3.1 | 112 |

Made From 350 fibers
Draw Temperature = ambient
*MFR = 18 as measured by ASTM Test Method D-1238

The results show that a higher draw ratio yields superior properties. The results also show that a smaller hole size (See Table 5) gives better properties. This is probably due to higher shear forces during the spinning process leading to high molecular orientation of the polymer molecules.

The optimum properties for this combination were obtained using polypropylene having an MFR of 36, and by processing the fibers at a high draw ratio and draw temperature from a small hole size.

EXAMPLE 3

Polyamide-Polyester (Core-Sheath)

A series of polyamide-polyester core-sheath bicomponent fibers was prepared as described above. For this set of experiments, nylon 6 (B-3) was the core and PCL (Tone® 767) was the sheath. The specific gravity of nylon 6(B-3) at 265° C. is 1. The core-sheath fibers were prepared at 80/20 to 35/65 core-sheath ratios at about 640 denier (1.8 denier per fiber) and processed at ambient to 50° C. draw temperature, 2.5 to 4 draw ratios; and 2.5 to 5 g/d tenacity. The fibers fused on-line, i.e., between zone 5 and roller 12 in the apparatus shown in FIG. 1, to form the monofilament tapes, similar to the PP-PCL core-sheath fibers, and required no subsequent processing in the apparatus shown in FIG. 2. The monofilament tapes were analyzed for mechanical properties. The results are shown in Tables 7A and 7B.

TABLE 7A

| Sample | Sheath PCL 767 | Core Nylon 6 | D/R | Draw Temp. | Denier | Breaking Load (lbs) | Tenacity (g/d) | Elong. (%) |
|---|---|---|---|---|---|---|---|---|
| 59 | 35 | 65 | 2.48 | 20 | 630 | 5.4 | 3.9 | 64 |
| 60 | 50 | 50 | 2.48 | 26 | 650 | 4.7 | 3.3 | 59 |
| 61 | 50 | 50 | 2.48 | 40 | 650 | 4.6 | 3.2 | 58 |
| 62 | 50 | 50 | 2.48 | 50 | 650 | 4.7 | 3.3 | 54 |
| 63 | 50 | 50 | 2.48 | 60 | 650 | 4.7 | 3.3 | 49 |
| 64 | 65 | 35 | 2.48 | 40 | 650 | 3.8 | 2.6 | 41 |
| 65 | 40 | 60 | 2.48 | 40 | 630 | 5.4 | 3.9 | 63 |

Made from 350 fibers

TABLE 7B

| Sample | Sheath PCL 767 | Core Nylon 6 | D/R | Draw Temp. | Denier | Breaking Load (lbs) | Tenacity (g/d) | Elong. (%) |
|---|---|---|---|---|---|---|---|---|
| 66 | 20 | 80 | 3.5 | 30 | 640 | 6.5 | 4.5 | 43 |
| 67 | 35 | 65 | 3.5 | 30 | 640 | 7.2 | 5.1 | 41 |
| 68 | 50 | 50 | 3.75 | 30 | 640 | 6.8 | 4.8 | 35 |
| 69 | 50 | 50 | 4 | 30 | 640 | 6.9 | 4.9 | 31 |
| 70 | 20 | 80 | 3.5 | 50 | 640 | 6.5 | 4.6 | 35 |
| 71 | 35 | 65 | 3.5 | 50 | 640 | 6.7 | 4.7 | 44 |
| 72 | 50 | 50 | 3.75 | 50 | 640 | 6.8 | 4.8 | 30 |

Elong. = elongation
Temp. = temperature (° C.)
D/R = draw ratio

The results show that a higher amount of nylon 6 gives higher tenacity values. For floss applications, 65% nylon 6 will provide enough strength and 35% PCL will provide adequate suppleness and bonding to the core fibers.

EXAMPLE 4

Polyamide-Poly(ether-amide) (Core-Sheath)

A series of polyamide-poly(ether-amide) core-sheath bicomponent fibers was prepared as described above. For this set of experiments, nylon 6 (B-3) was the core and Pebax® 4033 poly(ether-amide) commercially available through Elf Atochem was the sheath. The specific gravity of Pebax® 4033 was 1.05 at 240° C. The specific gravity of nylon 6(B-3) was 1.0 at 265° C. The fibers were made from 80/20 core-sheath ratios at 600–650 denier (1.7 to 1.85 deniers per fiber) at 2.3 draw ratio, 50° C. to 90° C. draw temperature and 3.5 to 5 g/d tenacity. The fibers did not fuse on-line, and post-treatment similar to Example 1 was required to fuse the Pebax® 4033 to form the final monofilament tape. The final monofilament tapes were analyzed for mechanical properties. The results are shown in Tables 8 and 9.

TABLE 8

| Sample | Sheath Pebax® 4033 | Core Nylon 6 | D/R | Denier | Breaking Load (lbs) | Tenacity (g/d) | Elong. (%) |
|---|---|---|---|---|---|---|---|
| 73 | 20 | 80 | 2.3 | 600 | 6.2 | 4.7 | 64 |
| 74 | 20 | 80 | 2.3 | 650 | 7.3 | 5.1 | 82 |
| 75 | 35 | 65 | 2.3 | 620 | 6 | 4.4 | 64 |
| 76 | 35 | 65 | 2.3 | 650 | 6.7 | 4.7 | 63 |
| 77 | 50 | 50 | 2.3 | 600 | 5.4 | 4 | 31 |
| 78 | 50 | 50 | 2.3 | 650 | 5.7 | 3.9 | 25 |
| 79 | 65 | 35 | 2.3 | 600 | 5 | 3.7 | 21 |
| 80 | 65 | 35 | 2.3 | 650 | 5.3 | 3.7 | 24 |

Made From 350 fibers
D/R = draw ratio
Elong. = elongation Draw
Temperature 50° C.

TABLE 9

| Sample | Sheath-Core Ratio | D/T | Total Draw | Breaking Load (lbs) | Tenacity (g/d) |
|---|---|---|---|---|---|
| 81 | 35/65 | 50 | 2.2 | 5.63 | 4.12 |
| 82 | 35/65 | 50 | 2.2 | 5.42 | 3.96 |
| 83 | 35/65 | 50 | 2.27 | 5.85 | 4.28 |
| 84 | 35/65 | 50 | 2.27 | 5.48 | 4.02 |
| 85 | 35/65 | 50 | 2.5 | 6.43 | 4.71 |
| 86 | 35/65 | 50 | 2.8 | 6.64 | 4.86 |
| 87 | 35/65 | 70 | 2.46 | 6.1 | 4.47 |
| 88 | 35/65 | 70 | 2.7 | 6.1 | 4.47 |
| 89 | 35/65 | 70 | 3 | 6.85 | 5.01 |
| 90 | 35/65 | 70 | 3.33 | 7.22 | 5.28 |
| 91 | 35/65 | 90 | 3.33 | 7.41 | 5.43 |

Made from 350 fibers
Sheath = Pebax ® 4033
Core = nylon 6
D/T = draw temperature (° C.)
Denier = 620

The results show that higher Pebax® 4033 content reduces the tenacity of the fibers, and that Pebax® 4033/nylon 6 fibers are stronger than the PCL/nylon 6 fibers. The results also show the tenacity of the fibers improved as a function of draw ratio and draw temperature. Thirty-five percent Pebax® 4033 bonded extremely well to the nylon 6 fibers, and provided superior suppleness and tenacity for dental floss applications.

EXAMPLE 5

Polyester-Poly(ether-ester) (Core-Sheath)

A series of polyester-poly(ether-ester) core-sheath bicomponent fibers was prepared as described above. For this set of experiments, PBT and PET were the core materials, and Hytrel® 4056 poly(ether-ester), commercially available through DuPont was the sheath material. The fibers were drawn according to the following sequence:

Undrawn fibers→first set of heated rollers (30–40 meters per minute; 50° C.)→hot water bath (70° C.)→second set of heated rollers (100–135 meters per minute; 50° C.) →steam oven→third set of ambient rollers (100–120 meters per minute)→take-up device.

The undrawn fibers were drawn between the first and the second set of heated rollers, and relaxed using the third set of rollers. Typical draw ratios for this operation were 2 to 4 and the denier of the drawn fibers were from 800–900. These fibers were fused to form monofilament tapes. The monofilament tapes were analyzed for mechanical properties. The results are shown in Tables 10A and 10B.

TABLE 10A

| Sample | Sheath Hytrel® 4056 | Core PBT | D/R | Denier | Breaking Load (lbs) | Tenacity (g/d) | Elong. (%) |
|---|---|---|---|---|---|---|---|
| 92 | 35 | 65 | 1.74 | 900 | 5.8 | 2.9 | 45 |
| 93 | 50 | 50 | 1.74 | 830 | 5.2 | 2.8 | 50 |

Made from 350 fibers
D/R = draw ratio
Elong. = elongation

TABLE 10B

| Sample | Sheath Hytrel® 4056 | Core PET | D/R | Denier | Breaking Load (lbs) | Tenacity (g/d) | Elong. (%) |
|---|---|---|---|---|---|---|---|
| 94 | 35 | 65 | 3 | 830 | 5.6 | 3.1 | 35 |
| 95 | 50 | 50 | 3 | 870 | 5.9 | 3.1 | 32 |
| 96 | 50 | 50 | On-Line | 830 | 5.2 | 2.8 | 26 |
| 97 | 65 | 35 | 2.63 | 900 | 4.2 | 2.2 | 27 |

Made from 350 fibers
D/R = draw ratio
Elong. = elongation

The results show that the tenacity values are not greatly affected by varying the Hytrel® 4056 content as was shown for other systems earlier.

EXAMPLE 6

(a) PET-PE (Core-Sheath)

A dental floss was made by applying a coating of Multiwax W-445 (Witco) microcrystalline wax to uncoated monofilament tape which had the following characteristics: 65/35 PET-PE core-sheath ratio; 600 Denier; 152 fibers; 3.94 denier/fiber; 0.05 mm thickness; 7.4 lbs breaking load; 5.6 g/d tenacity; 10% elongation at break.

The floss was made as follows: The monofilament tape was unwound from the supply spool, tensioned with a tensioner and passed through an eyelet. The wax coating, which was heated to 190° F., was applied to the monofilament tape via a die that was injected with the requisite amount of coating material. The monofilament tape was then passed through a chilled air tunnel and cooled to 37° F., and the resultant floss was rewound onto a take-up roll using conventional winding equipment. The floss contained a wax coating add-on of 18–20% based on the weight of the uncoated monofilament tape.

(b) Nylon 6-Pebax® 4033 (Core-Sheath)

A dental floss was prepared by the method described above with microcrystalline wax at an add-on of 18–20% based on the weight of the monofilament tape. The uncoated monofilament tape had the following characteristics: 65/35 nylon 6/Pebax® 4033 core/sheath ratio; 650 denier; 350 filaments; 1.85 denier/filament; 0.05 mm thickness; 6.7 lbs breaking load; 4.7 g/d tenacity; 60% elongation at break.

(c) Polypropylene (MFR 36)/PCL 767 (Core-Sheath)

A dental floss was prepared by the method described above [Example 6-(a)] with microcrystalline wax at an add-on of 18–20% based on the weight of the uncoated monofilament tape. The uncoated monofilament tape had the following properties: 65/35 polypropylene/PCL core/sheath ratio; 640 denier; 350 filaments; 1.82 denier/filament; 0.05 mm thickness; 6.5 lbs breaking load; 4.6 g/d tenacity; 27% elongation at break.

EXAMPLE 7

The above-mentioned monofilament tapes were also coated in the similar manner with the following compositions: microcrystalline wax—75–85%; spray-dried flavor—15–25%; and sodium saccharin—1%. The total add-on of the compositions was 35–45% based on the weight of the uncoated monofilament tape. Pebax® 4033/Nylon 6 monofilament tape did not feel waxy even when the add-on was as high as 44%. The high level of coating composition add-ons (i.e., 35–45%) makes it possible to more easily provide dental floss having increased levels of flavorants (thus providing "high flavor impact"), abrasives, active ingredients and other additives known in the art.

The dental flosses were tested for various properties including how the floss slides between teeth, shred resistance, strength, ease of use, effectiveness at cleaning, gentleness to gums, and clean feeling to mouth. The results are reported on a scale of from 0 to 10, with 0 being poor and 10 being excellent. The results are shown in Table 11.

TABLE 11

|  | PET/PE | Nylon 6/Pebax® 4033 |
|---|---|---|
| Overall Liking | 5.20 | 6.92 |
| High Quality | 5.27 | 7.44 |
| Sliding Easily Between Teeth | 5.89 | 7.61 |
| Not Shredding or Fraying Between Teeth | 6.38 | 7.67 |
| Not Breaking During Use | 7.24 | 8.09 |
| Strength of Floss | 6.62 | 7.86 |
| Being Gentle to Gums | 5.65 | 7.39 |
| Flexible/Not Stiff | 6.58 | 7.62 |
| Cleaning Teeth Effectively | 6.05 | 7.85 |
| Leaves Mouth Feeling Clean | 5.97 | 7.38 |
| Easy To Hold (Not Slipping) | 6.30 | 7.76 |
| Not Hurting/Causing Discomfort to Fingers While Using | 6.47 | 7.79 |
| Has the Right Thickness | 4.89 | 6.86 |
| Amount of Waxed Coating | 4.74 | 6.98 |
| Thickness (% "Just About Right") | 36% | 62% |
| Amount of Waxed Coating (% "Just About Right") | 36% | 56% |
| Appealing Appearance Before Use | 5.67 | 7.32 |
| Not Messy During Use | 6.24 | 7.91 |

The results above show that the monofilament tape flosses coated with 20% wax performed well in all attributes tested.

The surface and cross-section of the monofilament tapes were observed using scanning electron microscope. In all the monofilament tapes, the sheaths of the individual core/sheath filaments were fused during the calendering process. The cross-sections of the monofilament tapes also showed that the sheaths were fused along the length of the monofilament tapes.

The specific gravities at ambient temperature (approximately 22° C.) of the various polymers mentioned herein, as determined in accordance with the procedure set forth in ASTM Test Method D-792, are shown below.

| Polymer | Specific Gravity |
|---|---|
| Polyethylene terephthalate (PET) | 1.38 |
| Linear low density polyethylene (LLDPE) | 0.92 |
| Nylon 6 | 1.14 |
| Nylon 6,6 | 1.14 |
| Polypropylene (PP) | 0.9 |
| Pebax® 4033 | 1.01 |
| Polycaprolactone (PCL) | 1.14 |
| Hytrel® 4056 | 1.17 |
| Polybutylene terephthalate (PBT) | 1.42 |

We claim:

1. An article comprising: a bicomponent monofilament tape, said bicomponent monofilament tape comprising at least about 60 individual core fibers comprising a first polymer, each of said individual core fibers being individually surrounded by a sheath comprising a second polymer, wherein said bicomponent monofilament tape is substantially completely surrounded by the individual sheaths fused together.

2. The article of claim 1 wherein said bicomponent monofilament tape comprises from about 60 to about 600 individual core fibers.

3. The article of claim 1 wherein said bicomponent monofilament tape comprises from about 150 to 500 individual core fibers.

4. An article according to claim 1 wherein the denier of the individual core fibers ranges from about 0.6 to about 4.5.

5. An article according to claim 1 wherein the denier of the individual core fibers ranges from about 0.7 to about 3.8.

6. The article of claim 1 wherein the polymer comprising the individual cores is selected from a polyamide, a polyester, a polyolefin, and a fluorinated polymer.

7. The article of claim 6 wherein the polyamide is selected from the group consisting of nylon 6, nylon 11, nylon 12, and nylon 66; the polyester is selected from the group consisting of poly(ethylene terephthalate) and poly(butylene terephthalate); the polyolefin is selected from the group consisting of polypropylene and polyethylene; and the fluorinated polymer is poly(vinylidene fluoride).

8. The article of claim 7 wherein the polymer comprising the individual cores is selected from the group consisting of polypropylene and nylon 6.

9. The article of claim 1 wherein the polymer comprising the sheath is selected from a polyolefin; a polyester; a poly(ether-amide), a poly(ether-ester), an elastomer, and a poly(vinylidene fluoride) copolymer.

10. The article of claim 9 wherein the polyolefin is selected from the group consisting of polyethylene and polypropylene; the polyester is polycaprolactone; the poly(ether-amide) is selected from the group consisting of Pebax® 4033 SA polymer and Pebax® 7233 SA polymer; the poly(ether-ester) is selected from the group consisting of Hytrel® 4056 polymer and Riteflex® polymer; the elastomer is made from polyolefins, and is Engage® elastomers, the elastomer is made from a poly(ether urethane), and is Estane® elastomers, the elastomer is made from a poly(ester urethane), and is Estane® elastomers, the elastomer is made from poly(styrene-ethylene/butylene-styrene), and is Kraton® elastomers; and the poly(vinylidene fluoride) copolymer is KynarFlex® 2800 polymer.

11. The article of claim 10 wherein the polymer comprising the sheath is selected from the group consisting of polycaprolactone, polyethylene, Pebax® 4033 SA polymer, and Pebax® 7233 SA polymer.

12. The article of claim 1 wherein the ratio of core to sheath in the bicomponent core sheath fibers ranges from about 10 percent core and about 90 percent sheath to about 90 percent core and about 10 percent sheath.

13. The article of claim 12 wherein the ratio of core to sheath in the bicomponent core sheath fibers ranges from about 20 percent core and about 80 percent sheath to about 80 percent core and about 20 percent sheath.

14. The article of claim 13 wherein the ratio of core to sheath in the bicomponent core sheath fibers ranges from about 30 percent core and about 70 percent sheath to about 70 percent core and about 30 percent sheath.

15. The article of claim 1 wherein the thickness of the monofilament tape ranges from about 0.01 mm to about 0.15 mm.

16. The article of claim 15 wherein the thickness of the monofilament tape ranges from about 0.03 mm to about 0.07 mm.

17. The article of claim 1 wherein the monofilament tape has applied thereto a coating composition comprising a wax, a flavor and at least one other additive to form a dental floss.

18. The dental floss of claim 17 wherein the coating composition is present at from 15 weight percent to about 60 weight percent based on the weight of the monofilament tape; the flavor is selected from the group consisting of mint and cinnamon; and said at least one other additive is selected from the group consisting of sweeteners, abrasives, cleaners, chemotherapeutic agents, and whiteners.

19. A process comprising:
providing at least about 60 bicomponent core-sheath fibers; fusing the sheaths; and bonding the fused sheaths to the core fibers to form a monofilament tape.

20. The process of claim 19 wherein the core of the bicomponent core sheath fibers is selected from a polyamide, a polyester, a polyolefin, and a fluorinated polymer.

21. The process of claim 20 wherein the polyamide is selected from the group consisting of nylon 6, nylon 11, nylon 12, and nylon 66; the polyester is selected from the group consisting of poly(ethylene terephthalate) and poly(butylene terephthalate); the polyolefin is selected from the group consisting of polypropylene and polyethylene; and the fluorinated polymer is poly(vinylidene fluoride).

22. The process of claim 21 wherein the core of the bicomponent core sheath fiber is selected from the group consisting of polypropylene and nylon 6.

23. The process of claim 19 wherein the sheath of the bicomponent core sheath fibers is selected from a polyolefin; a polyester; a poly(ether-amide), a poly(ether-ester), an elastomer, and a poly(vinylidene fluoride) copolymer.

24. The process of claim 23 wherein the polyolefin is selected from the group consisting of polyethylene and polypropylene; the polyester is polycaprolactone; the poly(ether-amide) is selected from the group consisting of Pebax® 4033 SA polymer and Pebax® 7233 SA polymer; the poly(ether-ester) is elected form the group consisting of Hytrel® 4056 polymer and Riteflex® polymer; the elastomer is made from polyolefins, and is Engage® elastomers, the elastomer is made from a poly(ether urethane), and is Estane® elastomers, the elastomer is made from a poly(ester urethane), and is Estane® elastomers, the elastomer is made from poly(styrene-ethylene/butylene-styrene), and is Kraton® elastomers; and the poly(vinylidene fluoride) polymer is KynarFlex® 2800 polymer.

25. The process of claim 24 wherein the sheath of the bicomponent core sheath fibers is selected from the group consisting of polycaprolactone, polyethylene, Pebax® 4033 SA polymer, and Pebax® 7233 SA polymer.

26. The process of claim 19 wherein the ratio of core to sheath in the bicomponent core sheath fibers ranges from about 10 percent core and about 90 percent sheath, to about 90 percent core and about 10 percent sheath.

27. The process of claim 26 wherein the ratio of core to sheath in the bicomponent core sheath fibers ranges from about 20 percent core and about 80 percent sheath, to about 80 percent core and about 20 percent sheath.

28. The process of claim 27 wherein the ratio of core to sheath in the bicomponent core sheath fibers ranges from about 30 percent core and about 70 percent sheath, to about 70 percent core and about 30 percent sheath.

29. The process of claim 19 wherein the thickness of the monofilament tape ranges from about 0.01 mm to about 0.15 mm.

30. The process of claim 29 wherein the thickness of the monofilament tape ranges from about 0.03 mm to about 0.07 mm.

31. The process of claim 19 wherein the monofilament tape is coated with a coating composition comprising a wax, a flavor and at least one other additive to form a dental floss.

32. The dental floss of claim 31 wherein the coating composition is added at from 15 weight percent to 60 weight percent, based on the weight of the monofilament tape; the flavor is selected from the group consisting of mint and cinnamon; and the other additives are selected from the group consisting of sweeteners, abrasives, cleaners, chemotherapeutic agents, and whiteners.

* * * * *